US00PP08993P

United States Patent [19]

Machin

[11] Patent Number: Plant 8,993

[45] Date of Patent: Nov. 29, 1994

[54] CHRYSANTHEMUM PLANT NAMED PINK ARENA

[75] Inventor: Barrie J. Machin, Hants, England

[73] Assignee: Goldstock Breeding Limited, Hants, England

[21] Appl. No.: 138,238

[22] Filed: Oct. 19, 1993

[51] Int. Cl.[5] ..... A01H 5/00

[52] U.S. Cl. ..... Plt./80

[58] Field of Search ..... Plt. 76, 80

[56] References Cited

U.S. PATENT DOCUMENTS 4,616,099 10/1986 Sparkes ..... 47/58

OTHER PUBLICATIONS

Broertjes, et al., 1980, "A mutant of a . . . Irradiation of progressive radiation-induced mutants in a mutation breeding program with *Chrysanthemum morifolium*", Euphytica, 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and nose mutations induced by X-rays", Am. Soc. Hort. Sci. Proc., pp. 613–620.

Broertjes, 1966, "Mutation breeding of chrysanthemums", Euphytica, 15:156–162.

Dowrick et al., 1966, "The induction of mutations in Chrysanthemum using X- and gamma radiation", Euphytica, 15:204–210.

*Primary Examiner*—Howard J. Locker

*Attorney, Agent, or Firm*—Foley & Lardner

[57] ABSTRACT

A new Chrysanthemum cultivar named Pink Arena characterized the combined features of intermediate form, decorative type, light pink ray floret color, 90–110 mm capitulum diameter, 54–60 days flowering response period, plant height of 105–120 cm when grown with 14 long days prior to start of short days, and its inverted pyramid formation.

4 Drawing Sheets

1

The present invention comprises a new and distinct cultivar of chrysanthemum, botanically known as *Dendranthema grandiflora*, and referred to by the cultivar name Pink Arena.

Pink Arena is the product of a mutation induction program carried out by the inventor, Barrie J. Machin, in Fareham, England in 1986.

Pink Arena was discovered and selected by Barrie J. Machin in June 1986 as one flowering plant within a flowering block established as rooted cuttings from stock plants that had been exposed to an X-ray source of 1500 rads, in a controlled environment in Fareham, England. The irradiated parent cultivar was Arena, a cultivar developed by Barrie J. Machin from a breeding program in Fareham, England.

The first act of asexual reproduction of Pink Arena was accomplished when vegetative cuttings were taken from the selection in September 1986, by the inventor in a controlled environment in Fareham, England.

Horticultural examination of controlled flowerings of successive plantings has shown that the unique combination of characteristics as herein disclosed for Pink Arena are firmly fixed and are retained through successive generations of asexual reproduction.

Pink Arena has not been observed under all possible environmental conditions. The phenotype may vary somewhat with variations in environment such as temperature, light intensity and daylength, without, however, any variance in genotype.

The following observations, measurements and comparisons describe plants grown in Fareham, England under greenhouse conditions which approximate those generally used in commercial greenhouse practice.

2

The following traits have been repeatedly observed and are determined to be basic characteristics of Pink Arena, which, in combination, distinguish this Chrysanthemum as a new and distinct cultivar:

1. Intermediate capitulum form in which the outer ray floret petals are reflexing and the inner ray florets are incurving. The disc florets are not visible.
2. Decorative capitulum type.
3. Pink ray floret color.
4. Diameter across face of capitulum of 90–110 mm when fully opened.
5. Flowering response under normal temperatures is 54 to 60 days after start to short days.
6. Plant height is 105 to 120 cm when grown with 14 long days prior to start of short days.
7. Peduncle length of the first lateral at flowering after removing the apical bud and without growth regulator applications is 9.5 cm; peduncle length of the fourth lateral at flowering is 13.0 cm.
8. Flower formation is at approximately the same height since lower laterals are longer than upper laterals. This gives the effect of an inverted pyramid shape.

The accompanying photographic drawings show typical inflorescence and leaf characteristics of Pink Arena, with the colors being as nearly true as possible with illustrations of this type.

Sheet 1 is a color photograph of Pink Arena grown as a single stem spray cut mum.

Sheets 2 and 3 are black and white photographs showing the upper and under sides respectively of the leaves of Pink Arena in three stages of development (mature, intermediate and immature).

Sheet 4 is a black and white photograph showing three views of the inflorescence of Pink Arena.

Of the commercial cultivars known to the inventor, the most similar in comparison to Pink Arena is the cultivar identified as Dark Pink Gin, described in U.S. Plant Pat. No. 4,997. Reference is made to attached Chart A, which compares certain characteristics of Pink Arena with the same characteristics of Dark Pink Gin. Similar traits are capitulum form and type and spray formation. The ray floret color of both cultivars is described as pink but the ray floret of Pink Arena are a much paler pink color then the ray florets of Dark Pink Gin. In addition, Pink Arena has a larger diameter, faster flower response, and slightly greater peduncle height and length, based on plants of the respective cultivars being grown under similar conditions.

In comparison with the parent cultivar Arena, Pink Arena is similar thereto in all characteristics except ray floret color. The color of Pink Arena is a substantially redder pink than the pale pink of Arena.

In the following description, color references are made to The Royal Horticultural Society Colour Chart. The color values were determined on plant material grown as a single stem spray cut mum in Fareham, England in June 1986.

Classification:

*Botanical.*—*Dendranthema grandiflora* cv Pink Arena.

*Commercial.*—Decorative spray cut mum.

INFLORESCENCE

A. Capitulum:

*Form.*—Intermediate.

*Type.*—Decorative.

*Diameter across face.*—90–110 mm.

B. Corolla of ray florets:

*Color (general tonality from a distance of three meters).*—Pink.

*Color (upper surface).*—62D.

*Color (under surface).*—56D.

*Shape.*—Pointed.

C. Disc florets: There are typically few or no disc florets, and this varies from flower to flower. When disc florets are present, they are greenish yellow in color and small and tubular, containing male pollen-producing parts and female parts sufficient to form one seed. The presence or absence of disc florets appears to depend to some extent on growing conditions, with disc florets being relatively more common when plants are deprived of nutrition and grown in direct sunshine.

REPRODUCTIVE ORGANS:

*Androecium.*—None, where disc florets are not present; where disc florets do appear, they contain androecium sufficient to produce small amounts of pollen.

*Gynoecium.*—Present on all ray florets and on disc florets when present.

PLANT

A. General appearance:

*Height.*—105–120 cm.

B. Foliage:

*Color (upper surface).*—137B.

*Color (under surface).*—137C.

*Shape.*—See photograph.

CHART A

COMPARISONS MADE OF PLANTS GROWN AS SINGLE STEM SPRAY CUT MUMS IN FAREHAM, ENGLAND

| CHARACTERISTICS | PINK ARENA | DARK PINK GIN |
|---|---|---|
| Ray floret color | Pink | Pink |
| Capitulum form and type | Intermediate Decorative | Intermediate Decorative |
| Diameter across face of capitulum | 90 to 110 mm | 70 mm |
| Flowering Response | 54 to 60 days | 70 days |
| Pant height | 105 to 120 cm | 100 to 115 cm |
| Peduncle length: | | |
| 1st lateral | 9.5 cm | 8 cm |
| 4th lateral | 13.0 cm | 12 cm |
| Spray formation | Inverted Pyramid | Inverted Pyramid |

It is claimed:

1. A new and distinct Chrysanthemum plant named Pink Arena, as described and illustrated.

* * * * *

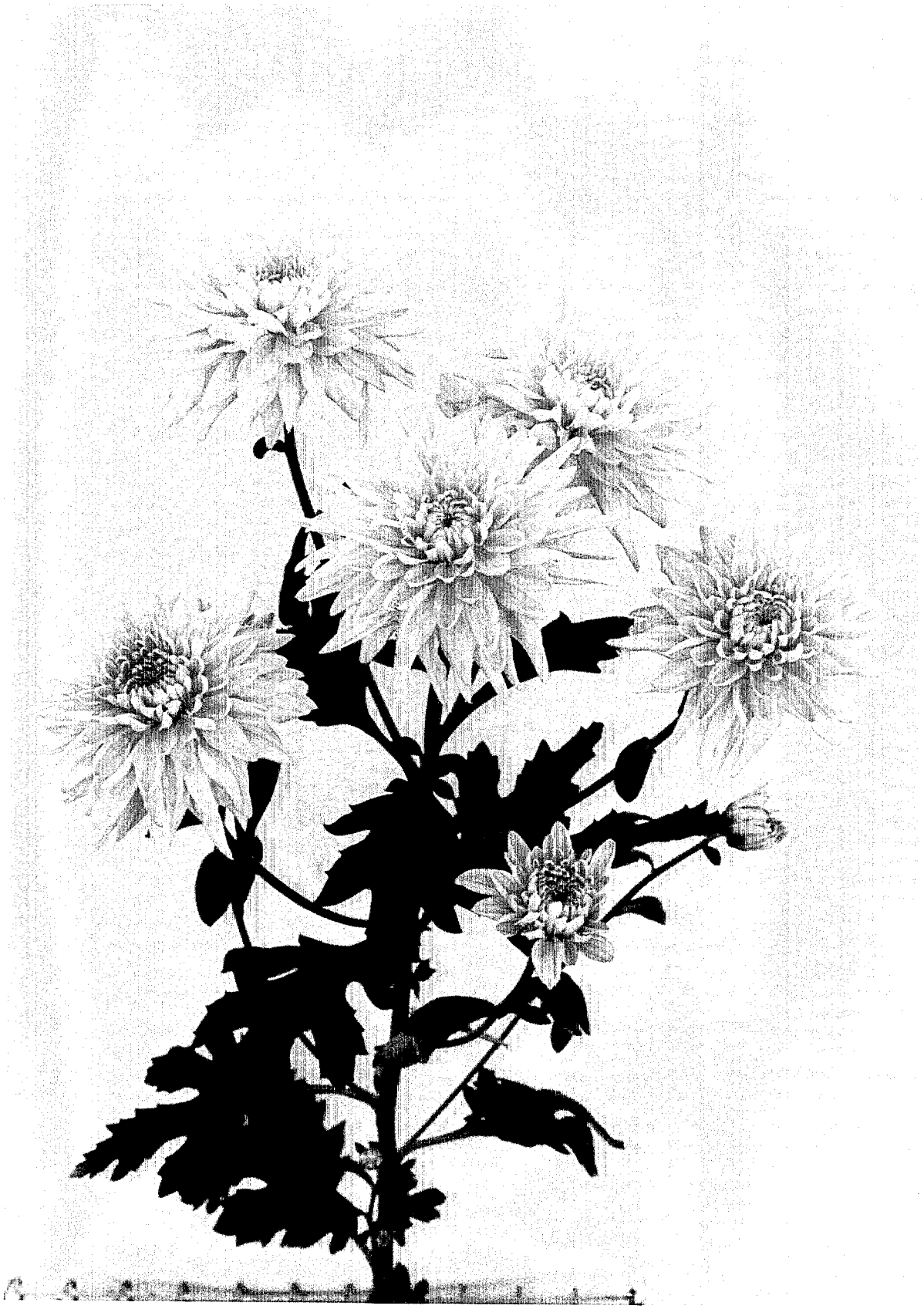

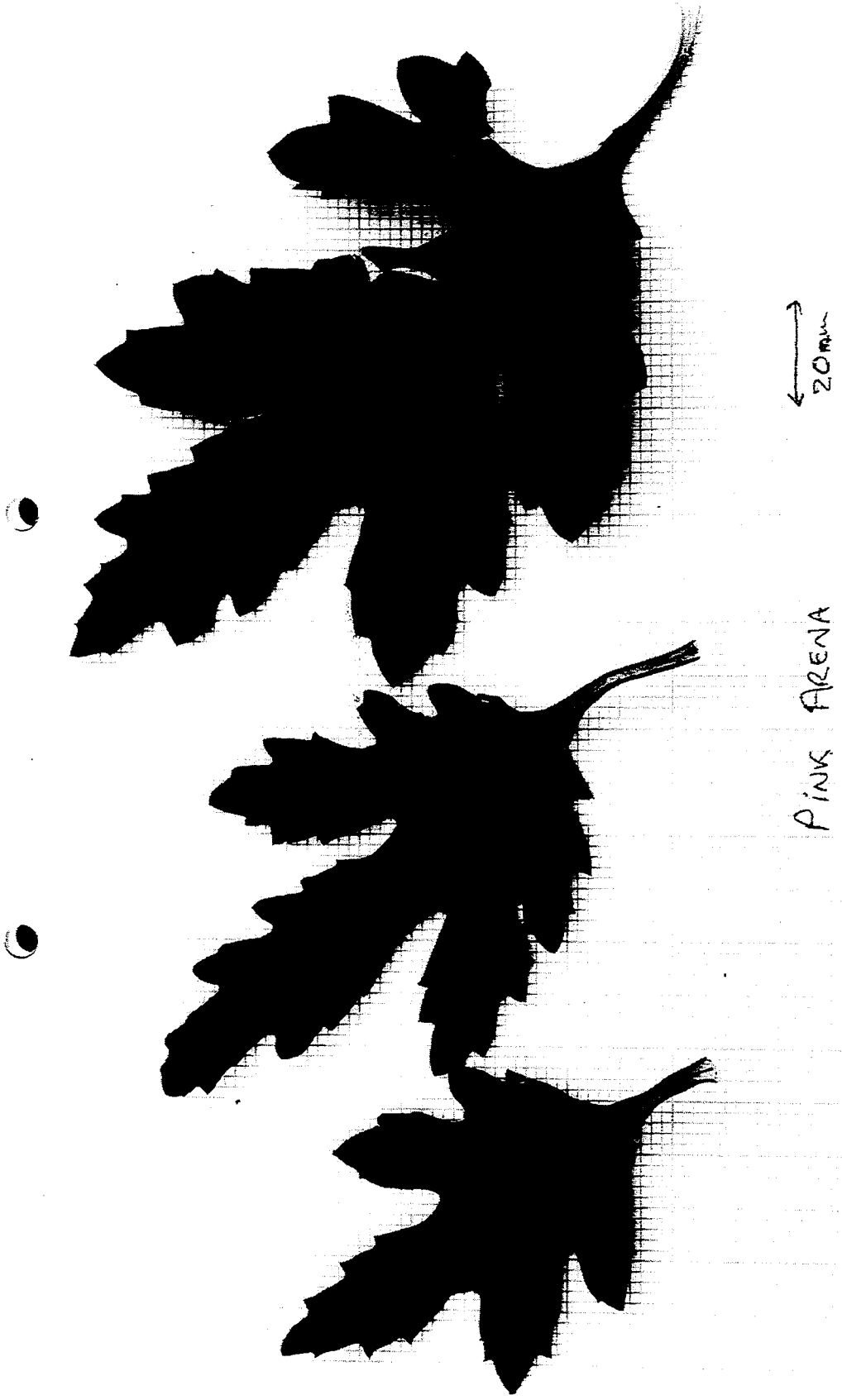
20mm
PINK ARENA

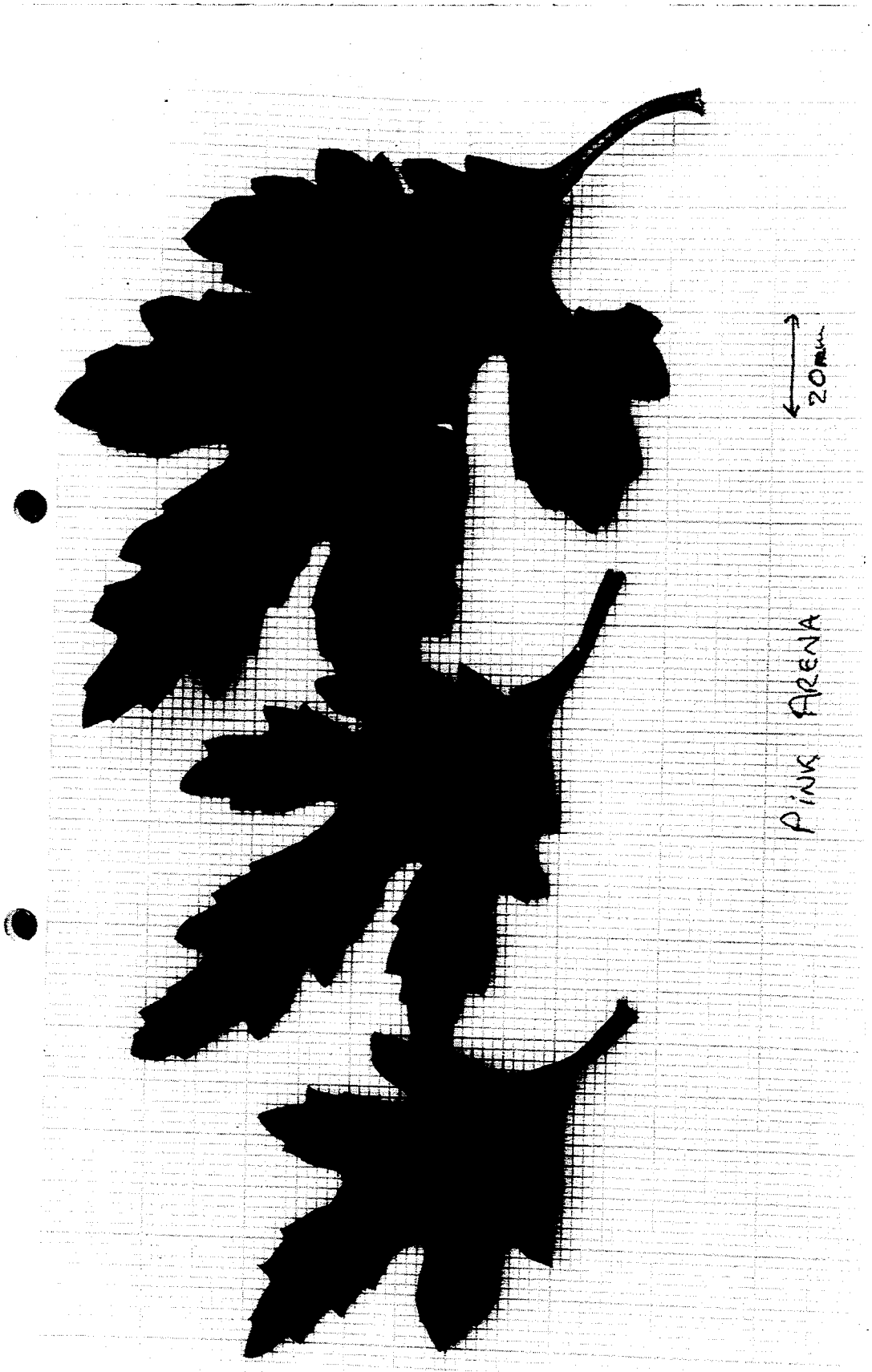
20mm
PINK ARENA

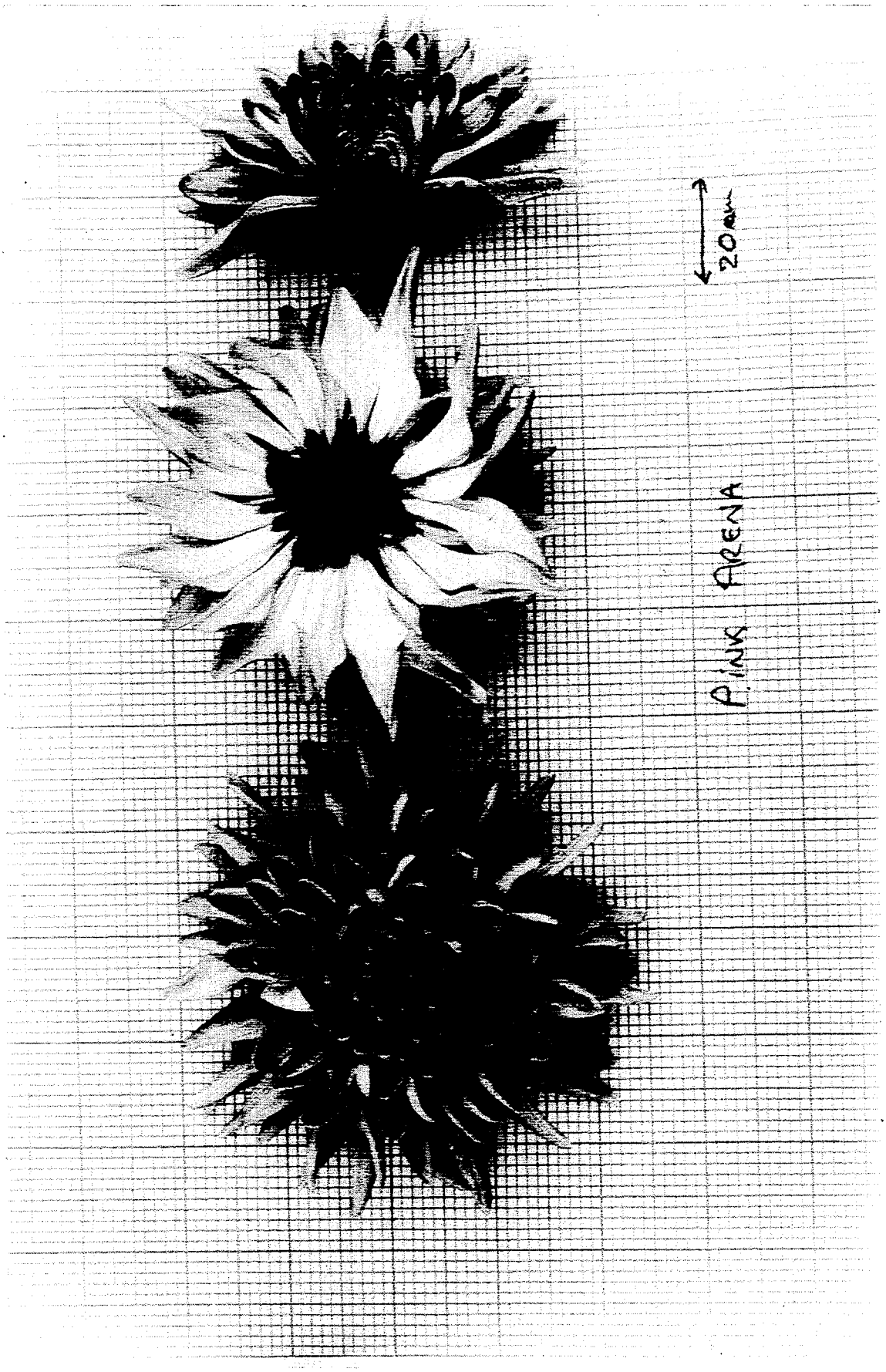
20 cm
PINK ARENA